(12) United States Patent
McLeod et al.

(10) Patent No.: US 8,575,126 B2
(45) Date of Patent: Nov. 5, 2013

(54) CONJUGATE CONSTRUCTS, DELIVERY, AND USE FOR TREATMENT OF DISEASE

(76) Inventors: Rima McLeod, Chicago, IL (US); Bo Shiun Lai, Chicago, IL (US); William Witola, Chicago, IL (US); Kamal El Bissati, Chicago, IL (US); Ernest Mui, Chicago, IL (US); Hong Moulton, Corvallis, OR (US); Jonathan B Rothbard, Menlo Park, CA (US); Jon D Moulton, Corvallis, OR (US)

( * ) Notice: Subject to any disclaimer, the term of this patent is extended or adjusted under 35 U.S.C. 154(b) by 0 days.

(21) Appl. No.: 13/507,427

(22) Filed: Jun. 27, 2012

(65) Prior Publication Data

US 2013/0053427 A1    Feb. 28, 2013

Related U.S. Application Data

(60) Provisional application No. 61/504,464, filed on Jul. 5, 2011.

(51) Int. Cl.
    *C12N 15/113*    (2010.01)
    *C07H 21/04*    (2006.01)

(52) U.S. Cl.
    USPC ........................... 514/44 A; 536/24.5

(58) Field of Classification Search
    None
    See application file for complete search history.

(56) References Cited

PUBLICATIONS

International Journal for Parasitology 2001, vol. 31, pp. 109-113.*

* cited by examiner

*Primary Examiner* — Tracy Vivlemore
(74) *Attorney, Agent, or Firm* — Richard D. Wood

(57) ABSTRACT

Pharmaceutical formulations of antisense peptide-conjugated phosphorodiamidate morpholino olgomers and methods of use for treatment of apicomplexan infections are disclosed. The invention is particularly directed to treatment of *Toxoplasma gondii* infections.

10 Claims, 9 Drawing Sheets

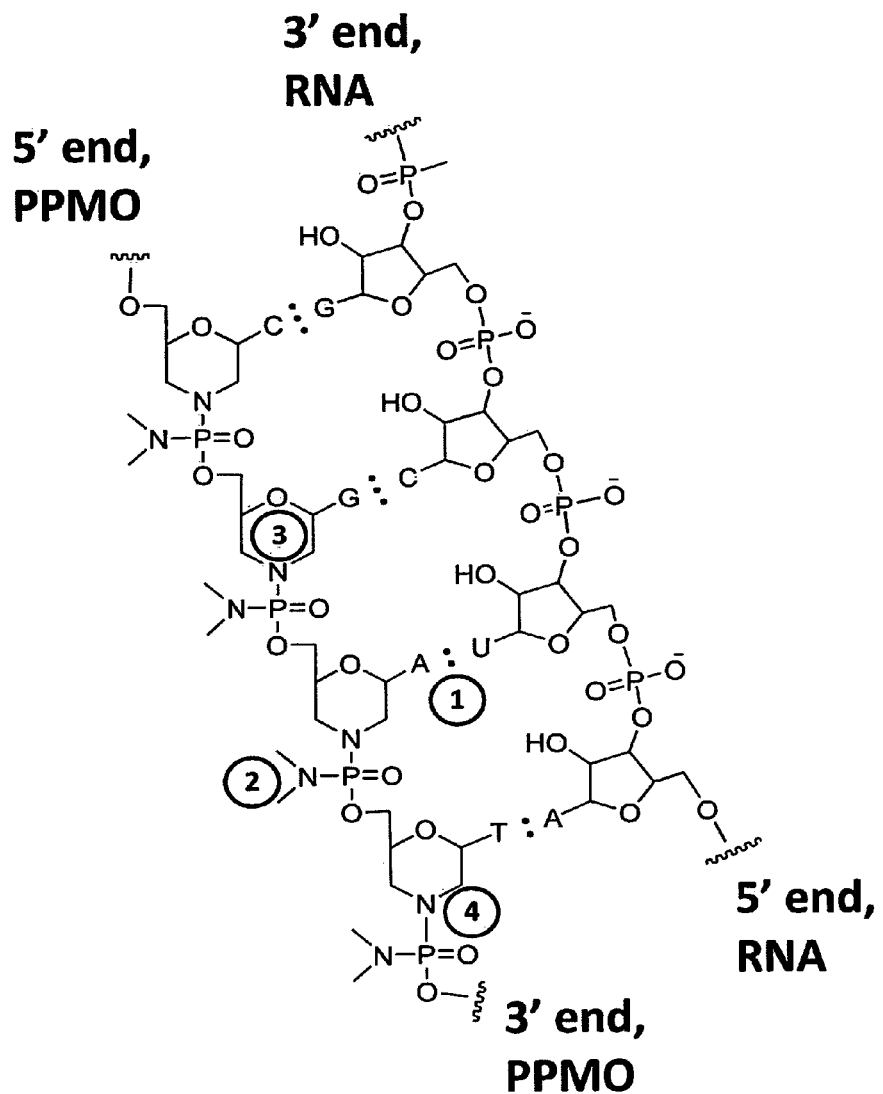
Figure 1. Structure of the oligonucleotide analog PPMO complexed through hydrogen bonds to a complimentary RNA strand

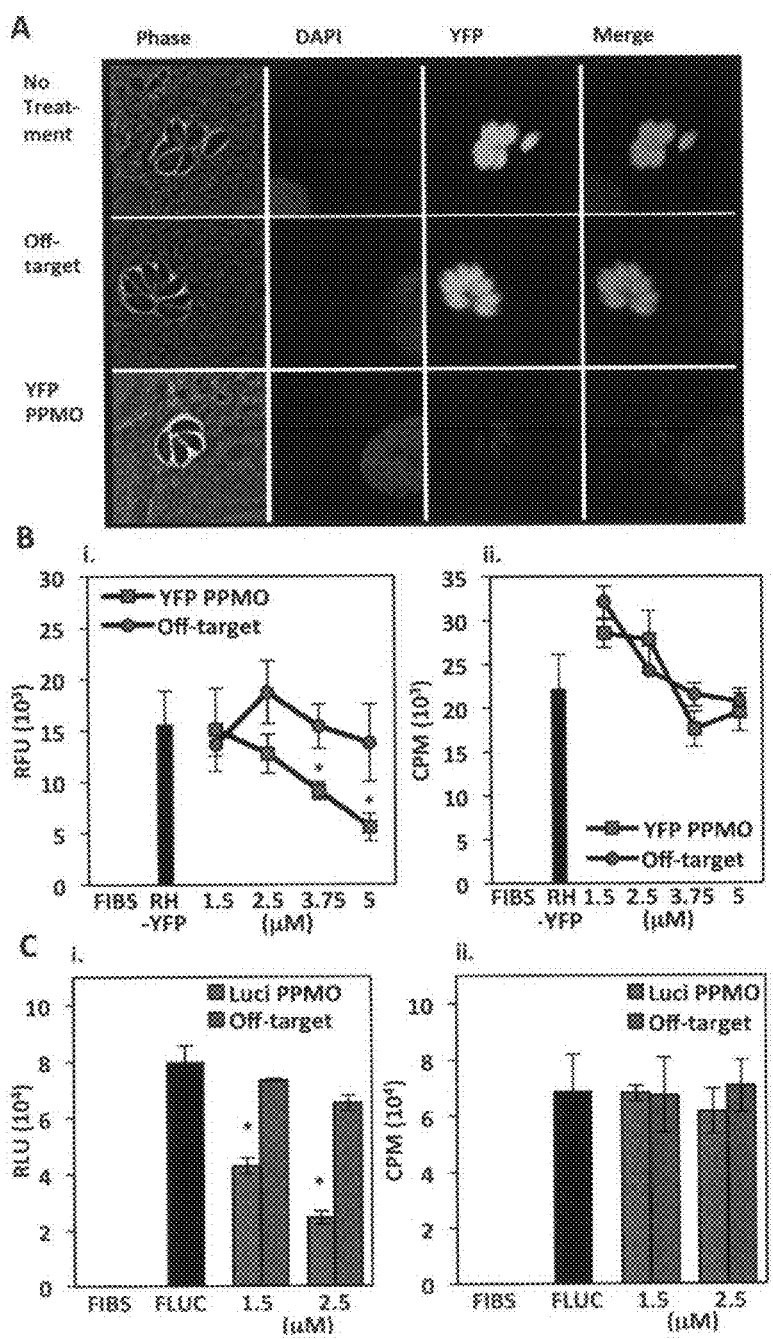
Figure 2. Effect of DHFR targeted PPMO on parasites and absence of effect of "off target" PPMO

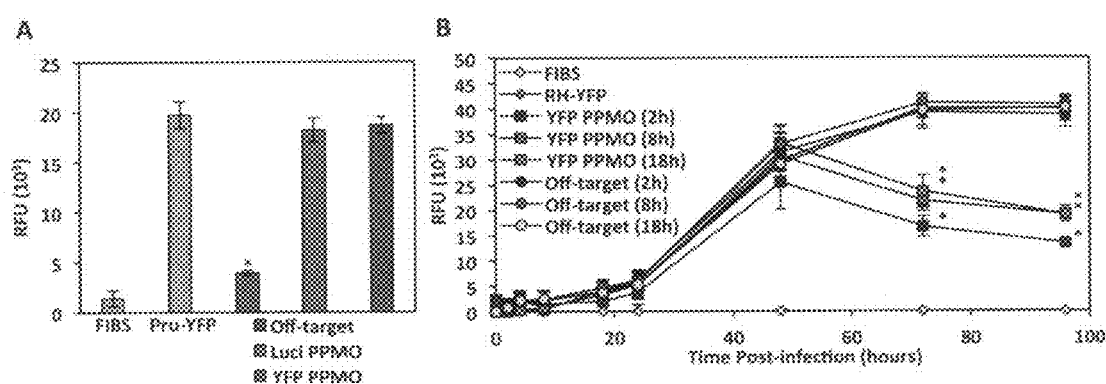
Figure 3. PPMO targeting YFP in Type II parasites

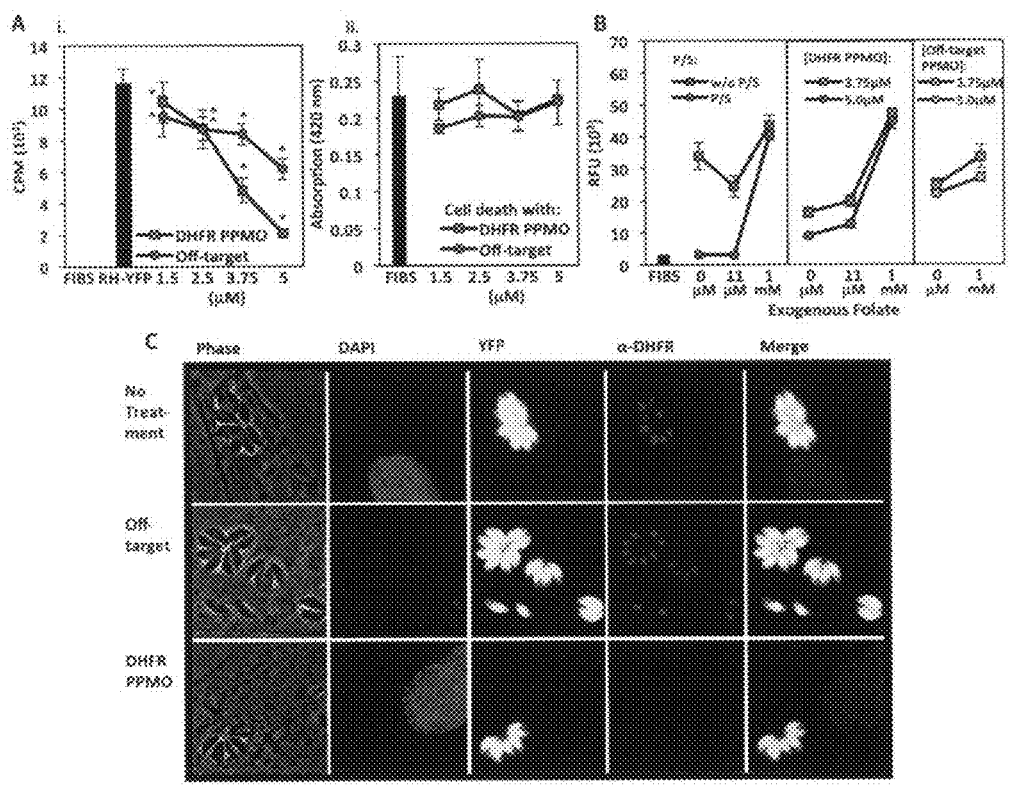
Figure 4. A: Effects of PPMO targeting DHFR on (i) parasite replication and (ii) HFF viability. B: RH-YFP parasites treated with pyrimethamine and sulfadiazine. C: Result of Immunofluorescence microscopy of PPMO against DHFR.

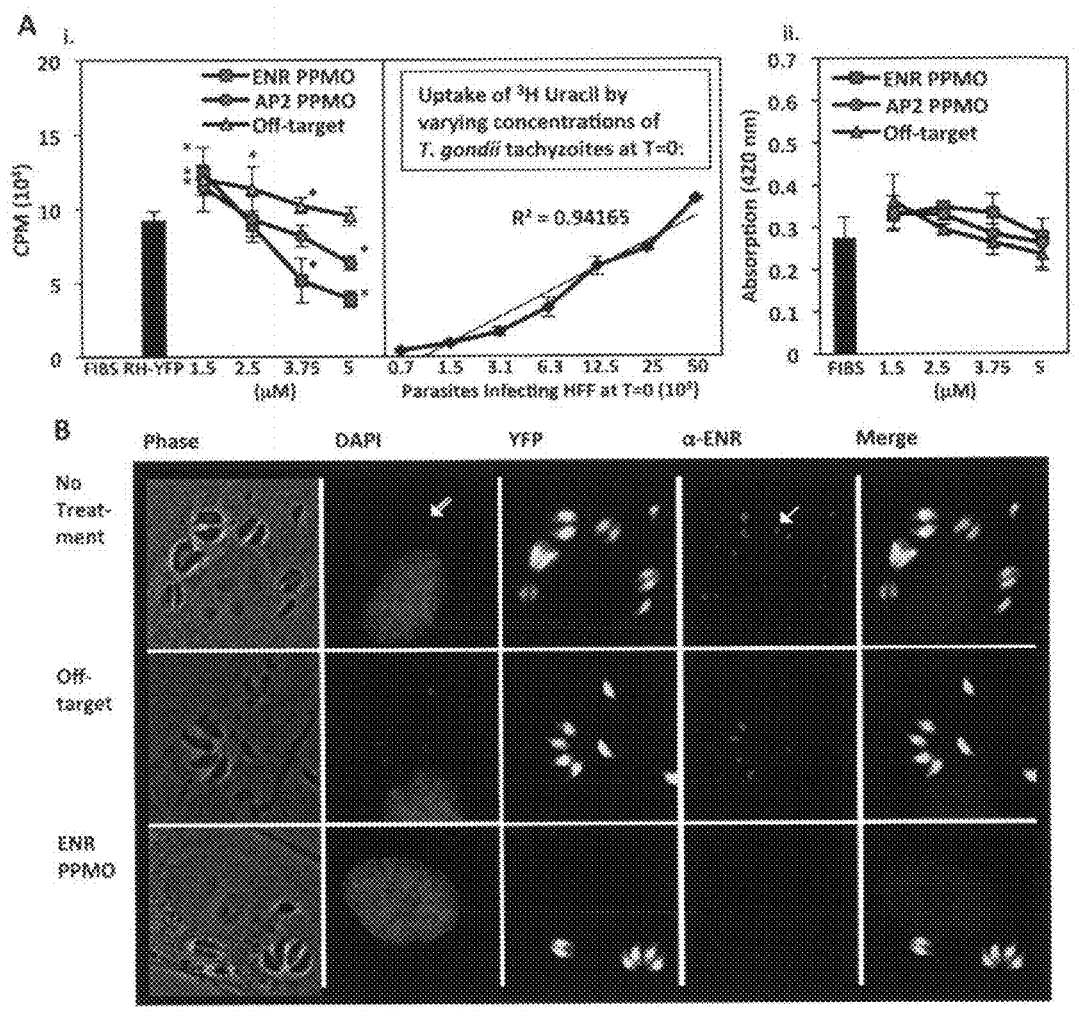
Figure 5.A: Effects of PPMO targeting ENR or AP2XI-3 on (i) parasite replication and (ii) HFF viability. B: Immunofluorescence staining confirming the efficacy of ENR-specific PPMO

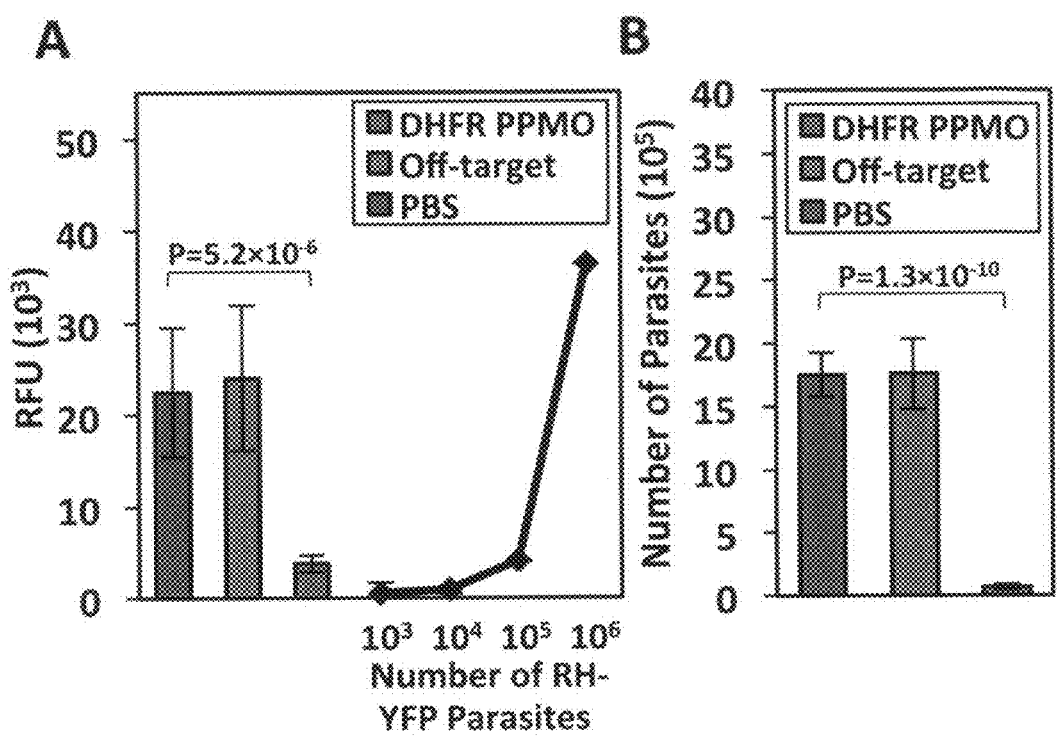
Figure 6. PPMO reduces parasite burden in vivo. Intraperitoneal fluid was harvested and quantified using (A) a fluorometer and (B) hemocytometer.

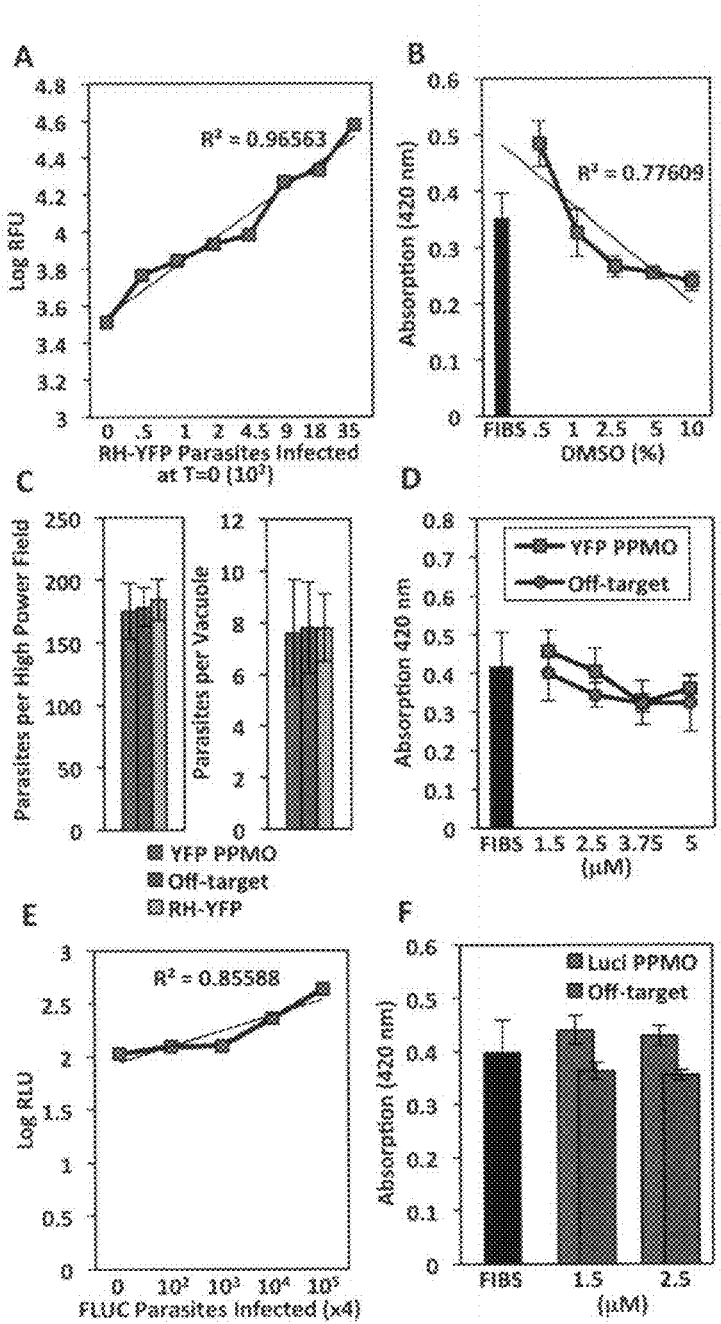
Figure 7. E effect of YFP PPMO and luciferase PPMO on stably transfected tachyzoits YFP and luciferase

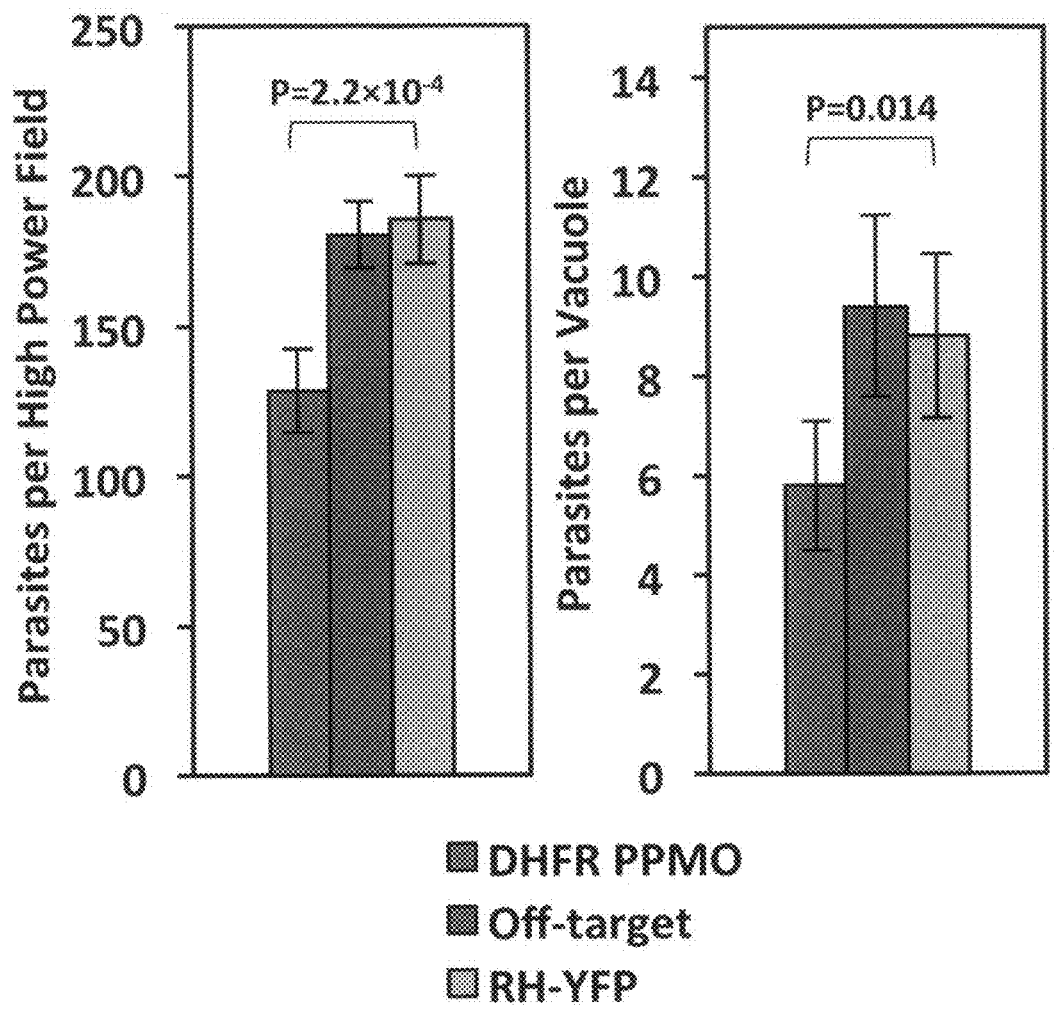
Figure 8. Effect of DHFR PPMO on mean number of parasites per vacuole and percent infected cells and lack of effect of off target PPMO

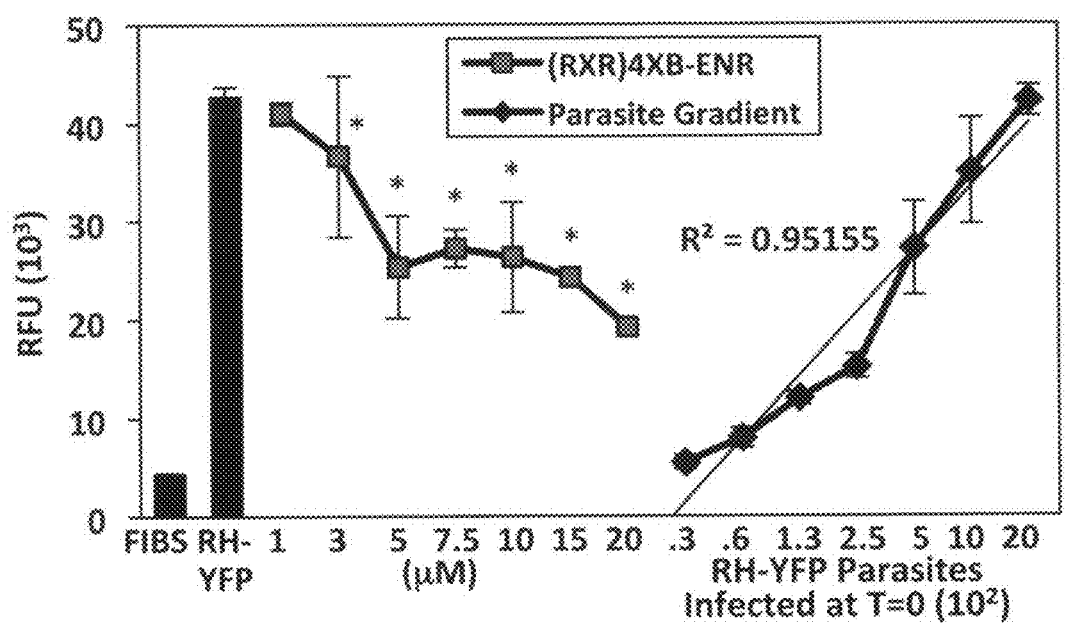
Figure 9. Effect of ENR PPMO with transductive peptide (RXR)₄XB has effect on replication in vitro without any toxicity to host cells to 30 µM.

CONJUGATE CONSTRUCTS, DELIVERY, AND USE FOR TREATMENT OF DISEASE

CROSS-REFERENCE TO RELATED APPLICATIONS

This application claims the benefit of U.S. Provisional Application No. 61/501,464 filed Jul. 5, 2011

STATEMENT REGARDING FEDERALLY SPONSORED RESEARCH OR DEVELOPMENT

This invention was made with Government support under grant NIAID NIH DMID AI012180 awarded by the National Institutes of Health. The Government has certain rights in this invention.

THE NAMES OF THE PARTIES TO A JOINT RESEARCH AGREEMENT

Not Applicable

BACKGROUND OF THE INVENTION

1. Field of the Invention

*Toxoplasma gondii* (hereinafter "*T. gondii*") is an apicomplexan parasite that chronically infects approximately one-third of the world's population. Disease caused by *T. gondii*, called toxoplasmosis, occurs in some infected persons. For example, when a pregnant woman acquires this infection for the first time during gestation, *T. gondii* can be transmitted congenitally to her fetus, causing death or severe ocular impairment and brain damage in the fetus. For most such persons infects the retina and/or brain. Recrudescence of the persistent encysted bradyzoites can then cause disease life-long. Infection in immune compromised persons also may cause severe, life threatening toxoplasmosis. This is a significant medical problem for persons with organ and stem cell transplantation, cancers, immunosuppressive medications and the acquired immunodeficiency syndrome.

The first line treatment of this disease is the combination of pyrimethamine and sulfadiazine. While highly effective against tachyzoites, these drugs may cause hematological side effects, other toxicities, and hypersensitivity. Further, no current drugs are effective in eliminating *T. gondii* bradyzoites in cysts. To cure *T. gondii* infections definitively, anti-toxoplasma medicines must cross the placenta, enter the retina, traverse the blood brain barrier as well as cyst walls and bradyzoite membranes. They also must cross the host cell membrane, the parasitophorous vacuole, and tachyzoite membranes. Improved drugs with significantly less toxicity, greater efficacy against tachyzoites and encysted bradyzoites, and access to infected tissues are urgently needed.

The general field of the invention is the production and use of pharmaceutical formulations comprised of oligonucleotide analogs, complex phosphorodiamidate morpholino olgomers, and complex phosphorodiamidate morpholino olgomers chemically coupled to specifically selected peptide sequences in order to prevent, inhibit, abrogate, mitigate, cure, or otherwise lessen the incidence or severity of disease. In one aspect, the field of the invention is the production and use of pharmaceutical formulations comprised of oligonucleotide analogs, complex phosphorodiamidate morpholino olgomers, and complex phosphorodiamidate morpholino olgomers chemically coupled to specifically selected peptide sequences in order to prevent, inhibit, abrogate, mitigate, cure, or otherwise lessen the incidence or severity of infection caused by apicomplexan parasites.

2. Description of Related Art

Antisense phosphorodiamidate morpholino olgomers (hereinafter "PMO") have been well studied as promising tools with potential to block ribonucleic acid transcription (Summerton, J; Weller, D (1997); Antisense & Nucleic Acid Drug Development 7 (3): 187-95), and as such have potential value as therapeutics whose purpose is to control protein expression. PMO designed as antibacterial agents (U.S. Pat. No. 6,677,153 to Iversen et al) and antiviral agents (U.S. Pat. No. 6,828,105 to Stein et al) have been disclosed. The ability of PMO to pass through cellular membrane structures so as to be available to interact with RNA targets is limited (Summerton, J. E.; (2007) Curr. Top. Med. Chem.; 7, 651-660). It has been shown that certain oligopeptides, in particular cationic oligopeptides, preferably arginine-rich oligopeptides, facilitate transport across membranes (Tzan, et al., (1993); American Journal of Physiology 265, No. 6, Part 1, pp. C1637-C1647). In addition, certain bioactive molecules, such as drugs, can be transported across membranes after chemical conjugation to some cationic oligopeptides (see for example U.S. Pat. No. 7,229,961 to Rothbard et al). It was disclosed that the cellular uptake of PMO chemically joined to selected cationic peptides is enhanced relative to the PMO alone (Moulton H, et al. (2004) Bioconjugate Chem 15:290-299). PMO conjugated to peptide (hereinafter "PPMO") having enhanced transport across cell membranes and enhanced antisense binding activity has been disclosed (U.S. Pat. No. 7,468,418 to Iversen et al). U.S. Pat. No. 8,067,571 to Weller et al disclosed PPMO with enhanced transport across cell membranes along with enhanced antibacterial activity and antisense binding activity. PPMO demonstrating enhanced transport across cell membranes along with enhanced antiviral activity and antisense binding activity was disclosed (U.S. Pat. No. 8,084,433 to Iversen et al). PMO or PPMO with oligonucleotide analog structures specifically engineered to interrupt RNA activity of apicomplexan parasites have not been reported. PMO or PPMO with oligonucleotides analog structures specifically engineered to identify, recognize, define, or validate molecular structures within or expressed by *T. gondii* have not been reported.

All citations are specifically incorporated by reference in their entirety for all purposes.

BRIEF SUMMARY OF THE INVENTION

The invention comprises methods of use of pharmaceutical compositions to treat diseases of the eye.

The invention is directed to an anti-apicomplexan antisense oligonucleotide analog of use in preventing or treating infections caused by apicomplexan parasites.

The invention is further directed to the production and administration of pharmacological formulations of PMO for the treatment of infections or related disorders caused wholly or in part by *T. gondii*.

The invention is further directed to the production and administration of pharmacological formulations of PPMO for the treatment of infections or related disorders caused wholly or in part by *T. gondii*.

The invention is further directed to the production and administration of pharmacological formulations of PMO for the treatment of infections or related disorders caused wholly or in part by *T. gondii* through the inhibition of enoyl-acyl carrier protein reductase.

The invention is further directed to the production and administration of pharmacological formulations of PMO for the treatment of infections or related disorders caused wholly or in part by T. gondii through the inhibition of AP2 domain transcription factor XI-3.

The invention is further directed to the production and administration of pharmacological formulations of PMO for the treatment of diseases of the eye including, but not limited to, adult macular degeneration, and retinopathy caused by over-expression of vascular endothelial growth factor or hypoxia-inducible factor.

The invention is further directed to the production and administration of pharmacological formulations of PPMO for the treatment of diseases of the eye including, but not limited to, adult macular degeneration, and retinopathy caused by over-expression of vascular endothelial growth factor or hypoxia-inducible factor.

The invention is further directed to the use of PMO chemical entities to identify, recognize, define, or validate the molecular target within or expressed by T. gondii which, upon inhibition, disruption, disassociation, or by another process is rendered dysfunctional by an anti-apicomplexan agent.

The invention is further directed to the use of PPMO chemical entities to identify, recognize, define, or validate the molecular target within or expressed by T. gondii which, upon inhibition, disruption, disassociation, or by another process is rendered dysfunctional by an anti-apicomplexan agent.

The anti-apicomplexan antisense oligonucleotide analog, also known as "morpholino", is comprised of a polymer built of from about 5 to about 50 morpholine-containing nucleotide analog monomers, preferably from 5 to 35 monomers, more preferably from 9 to 30 monomers, chemically joined through non-ionic phosphorodiamidate bonds. In one embodiment the optimal number of morpholine-containing nucleotide analog monomers which make up the PMO is 25. The PMO may be directed against RNA encoding one or more proteins expressed by and critical to the survival of the apicomplexan parasite including, but not limited to, dihydrofolate reductase (hereinafter "DHFR"), of enoyl-acyl carrier protein reductase, (hereinafter "ENR"), AP2 domain transcription factor XI-3 (hereinafter "AP2XI-3" or "AP-2"). The PMO may be directed against RNA encoding one or more non-parasite proteins which, if blocked or inhibited, ameliorate, mitigate, lessen, prevent, or treat diseases of the eye. These non-parasite proteins include, but are not limited to, vascular endothelial growth factor (hereinafter "VEGF") and hypoxia-inducible factor (hereinafter "HIF"). The nucleoside analogs in the PMO differ from those in ribonucleic acid in that the ribose ring is replaced by a morpholine, substituted at C2 (morpholine numbering) with a purine or pyrimidine nucleobase and at C6 with a hydroxymethyl group. The morpholine nitrogen is joined to the next morpholine analog in the 3' direction through a phosphorodiamidate bond. The hydroxymethyl is joined to the next morpholine analog in the 5' direction through a phosphorodiamidate bond.

BRIEF DESCRIPTION OF THE SEVERAL VIEWS OF THE DRAWINGS

FIG. 1 depicts the structure of the oligonucleotide analog PPMO complexed through hydrogen bonds to a complimentary RNA strand.

FIG. 2 shows the effect of DHFR targeted PPMO on parasites and absence of effect of "off target" PPMO.

FIG. 3(A) Depicts PPMO targeting YFP effective in Type II parasites stably transfected with YFP and an assay demonstrating kinetics of effect of PPMO. FIG. 3(B) shows the kinetics of YFP-specific PPMO.

FIG. 4 (A) depicts the effects of PPMO targeting DHFR on (i) parasite replication and (ii) HFF viability. FIG. 4(B) shows RH-YFP parasites treated with pyrimethamine and sulfadiazine. FIG. 4(C) is the result of immunofluorescence microscopy of PPMO against DHFR.

FIG. 5(A) shows the effects of PPMO targeting ENR or AP2XI-3 on (i) parasite replication and (ii) HFF viability. FIG. 5(B) depicts the immunofluorescence staining which confirmed the efficacy of ENR-specific PPMO.

FIG. 6 shows that PPMO reduces parasite burden in vivo. Intraperitoneal fluid was harvested and quantified using (A) a fluorometer and (B) hemocytometer.

FIG. 7 shows the effect of YFP PPMO and luciferase PPMO on stably transfected tachyzoite YFP and luciferase.

FIG. 8 depicts the effect of DHFR PPMO on mean number of parasites per vacuole and percent infected cells and lack of effect of off target PPMO.

FIG. 9 depicts the effect of ENR PPMO with transductive peptide $(RXR)_4XB$ has effect on replication in vitro without any toxicity to host cells to 30 µM.

DETAILED DESCRIPTION OF THE INVENTION

The terms below, as used herein, have the following meanings, unless indicated otherwise:

As used herein, the terms "compound", "agent", "oligomer" and "oligonucleotide analog" may be used interchangeably with respect to the antisense PMO of the claimed subject matter. As used herein, the terms "antisense oligonucleotide analog" or "antisense compound" are used interchangeably and refer to a sequence of subunits, each having a pyrimidine or purine nucleobase carried on a backbone subunit composed of a morpholino group, and where the backbone groups are linked by substantially uncharged phosphorodiamidate groups that allow the bases in the compound to hybridize to a target sequence in a apicomplexan RNA by Watson-Crick base pairing, to form an RNA:PMO heteroduplex within the target sequence. The PMO may have substantially complete complimentarity to the RNA target domain or near complimentarity so that the degree of complimentarity is in the range of about 80% to about 100%. PMO are designed to block or inhibit translation of the mRNA containing the target sequence.

The term "target sequence" refers to a portion of the target RNA against which the antisense agent is directed and will hybridize by Watson-Crick base pairing of an essentially complementary or nearly complementary sequence.

The term "targeting sequence" refers to the portion of the PMO which is substantially complimentary or nearly complimentary to the target sequence of the RNA to which the PMO is directed. The targeting sequence is determined by the process: 1) selection of an appropriate target protein, the disabling of which provides an advantage; 2) determination of the gene encoding that protein; 3) determination of the relevant mRNA sequence; 4) selection of the domain to which the antisense agent is directed. PMO can be directed to any mRNA sense sequence, and one embodiment of the present invention is the provision of PMO which block or inhibit the non-limiting group of proteins DHFR, ENR, AP2XI-3, VEGF, and HIF-1. Another embodiment of the invention is the provision of PMO to block or inhibit yellow fluorescent protein. Sequences of exemplary PMO are given in Table 1 as SEQ ID NO 1 through SEQ ID NO 8. It is clear to one with skill in the art that other PMO directed to the same or other vital apicomplexan proteins might be designed by fundamentally the same process and are considered within the scope of the present invention.

The term "transductive peptide" refers to a peptide, peptoid, or peptidomimetic which possesses the ability to enter into mammalian cells or microorganisms by crossing multiple membrane barriers. "Peptoid" refers to poly(N-substituted)glycines in which the side chain is bonded to nitrogen in the polymer backbone, rather than to the alpha carbon. The term "peptidomimetic" refers to peptide-like compounds into which unnatural elements have been introduced. Transductive peptides are chemically conjugated to the PMO to provide PPMO. An exemplary listing of transductive peptides is represented by SEQ ID NO 9 through SEQ ID NO 18 in Table 2. This listing is not meant to be limiting but rather to demonstrate that options for selection of the transductive peptide exist. The term "transductive peptide" as used herein also refers to dendrimeric molecular transporters designed to facilitate the delivery of PMO across membranes, such as VIVO-MORPHOLINO™ (Gene Tools, LLC, Philomath, Oreg.). The term "compound(s) of the invention" refers to compositions comprising PMO and PPMO specifically designed for prophylaxis or treatment of infection caused by apicomplexan parasites or specifically designed for prophylaxis or treatment of adult macular degeneration or specifically designed for prophylaxis or treatment of diabetic retinopathy.

The term "knock down" refers to the inhibition or blocking of protein synthesis due to steric inhibition of the transcription process. In one aspect of the present invention, said knock down is a result of Watson-Crick pairing of an antisense PMO to RNA encoding proteins essential to the elaboration of life-cycle processes in apicomplexan parasites, providing the prophylaxis or treatment of infection caused by said parasites. In another aspect of the invention, said knock down is a result of Watson-Crick pairing of an antisense PMO to RNA encoding proteins within or on the surface of the eye, wherein said PMO is specifically designed for the prophylaxis or treatment of diseases of the eye. It is recognized that in one aspect, PPMO of the invention, wherein PMO is conjugated to a transductive peptide, are specifically designed to knock down proteins essential to the elaboration of life-cycle processes in apicomplexan parasites, providing the prophylaxis or treatment of infection caused by said parasites. It is recognized that in another aspect, PPMO of the invention, wherein PMO is conjugated to a transductive peptide, are specifically designed to knock down proteins within or on the surface of the eye, wherein said PMO is specifically designed for the prophylaxis or treatment of diseases of the eye.

Compositions of PMO conjugated to a transductive peptide is specifically disclosed as one embodiment of the invention. The inventors point out that considerable experimentation was undertaken in order to deduce the PMO structures of SEQ ID NO 1 through SEQ ID NO 8, and to demonstrate their effectiveness. It is understood that conjugation of PMO directed against an apicomplexan parasite to a transductive peptide in order to facilitate transport across membranes with the express purpose of blocking or inhibiting parasite protein synthesis is an object of the present invention. Selection and evaluation of the transductive peptide best suited for practice of a specific embodiment of the invention, while not demanding an undue element of research, may need to be undertaken.

One non-limiting embodiment of the invention is a method of treatment comprising application of the conjugate represented by Structure 1, wherein the transductive peptide is the tetrameric repeat of RXR conjugated to the oligonucleotide analog PMO is the antisense phosphorodiamidate morpholino oligomer given in SEQ ID NO 1

(RXR) 4-AGCTAGATTCTAAAATGGTGAGCAAGGGCGAGC

1 wherein R is arginine, X is 6-aminohexanoic acid; and wherein the bases of the PMO are joined by morpholino phosphorodiamidate linkages.

*T. gondii* is an Apicomplexan parasite that chronically infects approximately one-third of the world's population. Disease caused by *T. gondii*, called toxoplasmosis, occurs in some infected persons. For example, when a pregnant woman acquires this infection for the first time during gestation, *T. gondii* can be transmitted congenitally to her fetus, causing death or severe ocular impairment and brain damage in the fetus (Boyer K, McLeod R (2002) in *Principles and Practice of Pediatric Infectious Diseases*, eds. Long, S., Proeber, C. & Pickering, L. (Churchill Livingstone, N.Y.), 2nd Ed., pp. 1303-1322). For most such persons infects the retina and/or brain. Recrudescence of the persistent encysted bradyzoites can then cause disease lifelong. Infection in immune compromised persons also may cause severe, life threatening toxoplasmosis. This is a significant medical problem for persons with organ and stem cell transplantation, cancers, immunosuppressive medications and the acquired immunodeficiency syndrome.

The current standard treatment of this disease is administration of pyrimethamine and sulfadiazine either separately or as a cocktail of the two. While highly effective against tachyzoites, these drugs may cause hematological side effects, other toxicities, and hypersensitivity (TenPas A, Abraham JP (1965); *Am J Med Sci* 249:448-453; Hakes T B, Armsstrong D (1983); *Cancer* 52:1535-1540; Caumes E, et al. (1995); *Clin Infect Dis* 21:656-658. Further, no therapies currently available are effective in eliminating *T. gondii* bradyzoites in cysts. To cure *T. gondii* infections definitively, anti-*Toxoplasma* drugs must cross the placenta, enter the retina, traverse the blood brain barrier as well as cyst walls and bradyzoite membranes. They also must cross the host cell membrane, the parasitophorous vacuole, and tachyzoite membranes. Improved medicines with significantly less toxicity, greater efficacy against tachyzoites and encysted bradyzoites, and access to infected tissues are urgently needed.

In addition, the development for new therapies against apicomplexan parasites can be facilitated by one embodiment of the invention wherein rapid and direct anti-sense PMO are utilized for target validation.

PMO (FIG. 1) are an anti-sense knockdown approach that disrupts mRNA translation. Because they inhibit their targets through Watson/Crick base-pairing mechanisms, PMO knockdown is a form of reverse genetic inhibition. The phosphorodiamidate groups on morpholino oligomers are neutral and hydrophilic, making PMO a highly stable and water-soluble inhibitory strategy. Because they contain stable phosphorodiamidate backbones, PMO can be stored at room temperature without degradation. PMO can be administered intravenously, intramuscularly and intranasally to insure delivery at the needed site of action. They also are non-toxic and non-immunogenic.

Transductive peptides attached to PMOs allow the oligomers to readily enter mammalian cells and microorganisms by crossing multiple membrane barriers (Morcos P A, Li Y, Jiang S (2008); *BioTechniques* 45:616-626). A transductive peptide has been shown to facilitate entry of molecular cargos into encysted, latent bradyzoites and deliver cargos across the blood brain barrier (Samuel B U, et al. (2003); *Proc Natl Acad Sci USA* 100:14281-14286; Kumar P, et al. (2007); *Nature*

448: 39-45). They also have been shown to deliver antimicrobial compounds to ocular tissues, such as the retina, optic nerve, and ocular epithelial tissues when applied topically (U.S. Pat. No. 7,229,961 to Rothbard, J. et al). Thus, transductive peptides' versatility, in combination with PMOs' stability, has potential promise for a variety of clinical applications (Svasti S, et al. (2008); *Proc Natl Acad Sci USA* 106: 1205-1210).

It is one aspect of the present invention to provide compositions comprising PMO designed as antisense constructs directed to specific domains in apicomplexan RNA. It is another aspect of the invention to provide compositions comprising PPMO designed as antisense constructs directed to specific domains in apicomplexan RNA, wherein said PPMO is the conjugate of PMO and a transductive peptide.

*T. gondii* can be transfected stably with yellow fluorescent protein (hereinafter "YFP") or luciferase, and the resultant engineered parasites produce YFP and luciferase, respectively. These proteins can be easily measured using standard reagents and techniques. Since YFP is a protein that, when excited at a certain wavelength, exhibits yellow fluorescence, it is easily quantifiable within intracellular parasites through a fluorometer or immunofluorescence analysis. Similarly, since luciferase is an enzyme that catalyzes luciferin to produce bioluminescence, inhibition of luciferase is quantifiable.

DHFR is an enzyme that is essential for the synthesis of *T. gondii* tetrahydrofolate, which is critical for production of purines, thymidylic acid and certain amino acids. Because DHFR is a known, validated anti-microbial target downstream from the *T. gondii* shikimate pathway (Roberts F, et al. (1998); *Nature* 393:801-805), it would be suitable as a next target in a proof of principle investigation.

ENR is involved in the type II fatty-acid biosynthesis (FAS) pathway in apicomplexan parasites such as *T. gondii* and *Plasmodium falciparum* (McLeod R, et al. (2001); *International Journal for Parasitology* 31:109-13). *T. gondii* ENR is a single polypeptide whereas the ENR activity in mammalian cells is subserved by a multidoman enzyme. These structural differences have been exploited in the development of antimicrobial agents effective against type II FAS (Muench S P, et al. (2006) *Acta Cryst D Biol Crystallogr.* 63:328-338). ENR is predominantly localized inside the *T. gondii* apicoplast, an organelle evolutionarily derived from and endosymbiotic algae and that has four surrounding membranes in *T.gondii*. Inhibiting ENR using PPMO would be a simple and direct way to determine whether ENR is essential (Ferugson D J P., et al. (2005) *Eukaryot Cell* 4:814-826; McFadden G I. (2011); *Photoplasma* 248:641-650) and a valid molecular target for future medicine development.

AP2XI-3 is a member of the plant-like Apicomplexan Apetela 2 (ApiAP2) transcription factor family (Behnke M, et al. (2010) *PLoS One* 5:e12354). ApiAP2 do not have homologues in mammalian cells. This family of ApiAP2 transcription factors regulates cell cycle, replication, and maintenance of the tachyzoite life cycle stage. These transcription factors also regulate differentiation, and switch to and maintenance of the bradyzoite life cycle stage in Apicomplexan parasites (De Silva E K, et al. (2008); *Proc Natl Acad Sci USA* 105: 8393-8398). AP2XI-3 is believed to play a key role in tachyzoite replication.

Transcription factors have been considered difficult to target because they are intracellular proteins which bind to a short DNA motif that could occur in multiple species including humans. Successful specific inhibition of AP2XI-3 through PPMO would is of considerable value because the anti-sense approach is used to abrogate transcription factors, which are difficult to target through other means. Transcription factors of interest are essential for sustaining tachyzoites and encysted bradyzoites such as Apetela 2 transcription factors. Three transcription factors are important for maintaining the tachyzoite stage, and three transcription factors are important for maintaining the bradyzoite stage.

Applying PPMO enables the determination of whether either or both ENR and AP2XI-3 are essential for tachyzoites. This establishes whether the enzyme and transcription factor are promising targets for future medicine development and useful tools to study their biological functions.

Knockdown of transfected YFP resulted in diminished fluorescence. Immunofluorescence staining was conducted to visualize YFP knockdown (FIG. 2A). Human foreskin fibroblasts (HFF) were infected with Type I RH parasites that were stably transfected with YFP. Wild-type parasites were treated with YFP-specific PPMO, and the anti-sense oligomers showed no observable effects on intracellular tachyzoites' fluorescent intensities in comparison to those of untreated parasites. However, YFP stably transfected parasites treated with YFP-specific PPMO showed reduced amounts of fluorescence. Both off-target and YFP-specific PPMO did not adversely hinder the parasites' ability to invade HFF.

In addition to being qualitatively assessed, YFP fluorescence also was standardized using increasing concentrations of YFP-transfected parasites and measuring amounts of fluorescence using a fluorometer. The fluorometer detected increasing amounts of RH-YFP parasites, with a strong, positive correlation between the number of stably transfected RH-YFP parasites and their fluorescence 96 hours after infection ($R^2=0.97$).

Effect of PPMO on HFF viability was studied (FIG. 7). HFF viability was quantifiable using a novel WST-1 cell proliferation assay. This assay was standardized with increasing dimethyl sulfoxide (DMSO) concentrations. Concentrations less than 1% were not toxic, but concentrations over this amount were toxic to HFF, with greater toxicity at higher concentrations. The WST-1 cell proliferation assay could detect decreasing HFF viability by staining for formazan production in host cells' mitochondria ($R^2=0.78$). The WST-1 cell proliferation assay was able to distinguish HFF grown under toxic conditions from those that were not, as the HFF grown in media containing 1% DMSO and 0.5% showed no toxicity. In contrast, those grown in media containing more than 1% DMSO were less viable. This assay was utilized herein to assess each PPMO's effect on HFF viability.

Fluorescence intensities were quantified to corroborate the effectiveness of YFP-specific PPMO against fluorescence (FIG. 2Bi). HFF infected with 2,000 RH parasites stably transfected with YFP but not treated with any PPMO had 15,065 Relative Fluorescence Units (RFU) 96 hours post-infection (FIG. 2Bi). Fluorescence diminished with increasing concentrations of YFP-specific PPMO. When parasites stably transfected with YFP were treated with 3.75 μM and 5 μM of YFP-specific PPMO, fluorescence was reduced by 40% and 63% respectively, 96 hours post-infection. These reductions were statistically significant when compared with untreated RH-YFP parasites (At 3.75 μM, P=0.021; At 5 μM, P=0.0049). Off-target PPMO did not have an inhibitory effect on intracellular tachyzoites' fluorescence in comparison to infected fibroblasts without PPMO (P=0.47).

PPMO with mutations were not effective in reducing fluorescence. For example, for cultures treated with PPMO with a mismatched sequence that contained 13 point mutations, at a concentration of 3.75 μM, there were 4,414±463 RFU, and similarly, untreated control cultures had 4,777±1,358 RFU (P>0.05).

Uracil is utilized by *T. gondii* but not by mammalian cells (Mui E, et al. (2005); *Antimicrob. Agents Chemother.* 49:3463-3467), so its utilization reflects parasite replication and survival. Uracil uptake was assayed to examine effects of PPMO on tachyzoites' replication (FIG. 2B ii). Average uracil uptake of parasites treated with 5 μM of YFP-specific PPMO, was 19,466±1,477 Counts per Minute (CPM), that did not differ from uracil uptake of untreated YFP parasites (P=0.16). Parasites treated with off-target PPMO also had comparable amount of uracil uptake, measured at 20,638±2,140 CPM, as untreated *T. gondii* stably transfected with YFP (P=0.27). Pair wise statistical tests between on-target and off-target PPMO results yielded no difference (P>0.05.) Further measurement of mean number of parasites per vacuole and percent infected cells evaluated using a microscope did not differ (FIG. 7C). The WST-1 cell proliferation assay was conducted to measure PPMO's effect on HFF host cell viability (FIGS. 7B and 7D). Absorption of formazan dye with 1.5 μM, 2.5 μM, and 3.75 μM of YFP-specific PPMO and all off-target PPMO's concentrations tested were not lower than the absorption of untreated HFF 96 hours post-infection (FIG. 7D, P>0.05 for all comparisons). Pair wise statistical tests conducted showed that no significant difference between the corresponding on-target and off-target PMO results (P>0.05).

Knock down of transfected luciferase reduces parasite luminescence. The luciferase-luciferin interaction was standardized to distinguish various concentrations of Prugneaud Type II parasites stably transfected with luciferase (FIG. 7E). The assay was successful in distinguishing different numbers of Type II Prugneaud parasites stably transfected with firefly luciferase (FLUC); the level of luminescence had a positive correlation with increasing numbers of luciferase-transfected tachyzoites ($R^2$=0.88) (FIG. 7E). This standardized assay was then utilized to measure effects of luciferase-specific PPMO in knocking down luciferase gene expression in tachyzoites. HFF were infected with 3,500 FLUC and were treated with 2.5 μM of luciferase-specific PPMO. Luminescence was significantly reduced from 65,162 Relative Luminescence Units (RLU) in untreated parasites to 24,517 RLU 96 hours post-infection among those treated with luciferase-specific (P=0.0082) (FIG. 2Ci). Off-target PPMO had no effects on parasite luminescence at 2.5 μM and 1.5 μM compared with untreated parasites (P=1.00 and P=0.38 respectively) (FIG. 2Ci). Parasite and host cell viability assays were conducted using luciferase-specific PPMO (FIG. 2C ii; FIG. 7F). It was found that luciferase-specific and off-target PPMO had no adverse effects on parasites' uracil incorporation and HFF's formazan production in the mitochondria compared with HFF not grown in DMSO-containing media (P>0.05 for all comparisons).

Knock down of transfected YFP in different parasite strains demonstrates efficacy in genetically diverse parasites known to have different virulence. To investigate the effects of PPMO targeting YFP in a strain other than RH Type I *T. gondii*, YFP-specific PPMO were applied to abrogate YFP expression in Prugneaud Type II parasites stably transfected with YFP instead of RH Type I *T. gondii* (FIG. 3A). To test whether active PPMO not targeting YFP would have off-target effects, luciferase-specific oligomers, in addition to off-target PPMO, were utilized as a control. HFF infected with 3,500 Prugneaud Type II parasites stably transfected with YFP had 19,714±1,331 RFU 96 hours post-infection. Parasites treated with 3.75 μM of YFP-specific PPMO showed an 80% reduction in fluorescence compared with untreated infected cultures (P<0.05) (FIG. 3A). Type II parasites treated with luciferase-specific or off-target anti-sense PPMO had RFU of 18,207±1,168 and 18,729±829, respectively. Their luminescence was not significantly different from untreated Type II Prugneaud parasites (P=0.13 and P=0.32, respectively).

Kinetics of YFP-specific PPMO. YFP-RH tachyzoites were treated with 3.75 μM YFP-specific and off-target PPMO at 2 h, 8 h, or 18 h post-infection to investigate the kinetics of PPMO against YFP expression. Effects of PPMO cultured at 2 h targeting YFP was particularly noticeable from 48 h to 72 h, decreasing from 25,596±5,413 to 16,682±1,960 RFU over this period, as were PPMO added at 8 h and 18 h post-infection. Off-target PPMO did not have conspicuous effects on YFP expression throughout the 96-hour time span.

Knock down of native DHFR inhibits parasite replication. PPMO targeting endogenous DHFR were cultured with HFF infected with stably transfected YFP parasites to determine the efficacy of the anti-sense oligomers on a known, essential molecular target (FIG. 4Ai). Mean SD CPM of uracil uptake at 96 hours post-infection when 3.75 μM and 5 μM of DHFR-specific PPMO were administered were, respectively, 20,875±2,417 and 48,283±7,799. These counts were significantly lower than the CPM of untreated parasites (At 3.5 μM, P=0.009; At 5 μM, P=0.009). They were also 52.4% and 66.2%, respectively, lower than the CPM of off-target PPMO at the same concentrations. Further measurement of mean number of parasites per vacuole and percent-infected cells evaluated using a microscope were lower (FIG. 8; p<0.05). Absorption of formazan dye at all concentrations of both DHFR and off-target PPMO were not statistically distinguishable from the absorption of untreated HFF (P>0.05 for all values) (FIG. 4A ii).

To study the specificity of PPMO targeting DHFR, knockdown of DHFR was product rescued with exogenous folic acid (FIG. 4B). Untreated RH Type I parasites stably transfected with YFP were used as a control. They exhibited 33,956±4,290 RFU 96 hours post-infection. With 1.13 mM of exogenous folic acid, untreated YFP parasites had 43,544±3,148 RFU 96 hours after infection. Pyrimethamine also targets DHFR, so rescuing parasites treated with pyrimethamine and sulfadiazine also served as a control. Parasites treated with pyrimethamine and sulfadiazine were fully rescued with 1.13 mM of folic acid, displaying 40,274±1,305 RFU 96 hours post-infection. Similarly, 1.13 mM of folic acid fully rescued parasites treated with 3.75 μM and 5 μM of DHFR-specific PPMO. Without folic acid, parasites that were treated with 3.75 μM and 5 μM of PPMO targeting DHFR had 16,429±1,589 RFU and 9,058±709 RFU, respectively, 96 hours post-infection. With folic acid, parasites showed parasites treated with 3.75 μM and 5 μM of DHFR-specific PPMO showed 47,478±1,406 RFU and 44,957±2,448 RFU, respectively. In comparison to the dramatic rescuing effects of exogenous folic acid on parasites treated with DHFR inhibitors, folic acid had minimal effects on the viability of parasites treated with either 3.75 μM or 5 μM of off-target PPMO.

Immunofluorescence assay (FIG. 4C) was conducted to not only visualize the effect of knock down but also substantiate the specificity of PPMO targeting endogenous DHFR. After 48 hours of treatment with DHFR-specific PPMO, DHFR expression among intracellular parasites exhibited marked reductions. Off-target PPMO had no effects on DHFR expression. Both DHFR and off-target PPMO had no effect on YFP expression.

Knock down of ENR and AP2XI3 establishes that they contribute to parasite replication. PPMO were further studied to determine whether they could knockdown ENR and AP2XI-3 protein production and thereby to determine whether they contribute to parasite replication (FIG. 5A left panel). While at 3.75 μM and 5 μM off-target PPMO had insignificant effects on parasite viability (P=0.83 and P=0.057 respectively), PPMO specific to ENR or AP2XI-3 resulted in reductions in parasite replication at 3.75 µM and 5 µM 96 hours post-infection (FIG. 5Ai, left panel, P<0.05 for all values). Cultures with increasing concentrations of parasites were studied at 96 hours post-infection to determine whether this assay could differentiate these parasite concentrations. This assay could discriminate between these numbers of parasites (FIG. 5A, right panel, $R^2$=0.9416).

WST-1 cell proliferation assay was performed to assess effects of PPMO targeting ENR and AP2XI-3 on HFF viability (FIG. 5A ii). Active and off target PPMO had no noticeable toxicity on HFF at all concentrations tested, since all absorption values were above untreated HFF and absorption values of ENR— and AP2-specific PPMO were statistically indistinguishable with respect to their corresponding off-target PPMO concentrations (P>0.05 for all comparisons).

Immunofluorescence assays (FIG. 5B) demonstrated that expression of ENR was localized to the tachyzoites' apicoplast. They also demonstrated that PPMO specific to *T. gondii* ENR robustly knocked-down enzyme without adversely affecting YFP expression, while off-target PPMO did not abrogate ENR. Further, $(RXR)_4BX$ peptide as part of ENR PPMO is effective and not toxic at 20 µM (FIG. 9).

PPMO targeting DHFR reduce parasite burden in infected mice. Mice infected with YFP-transfected RH parasites were treated with PPMO targeting DHFR (FIG. 6) to determine whether PPMO were effective in vivo. Intraperitoneal fluid was collected and quantified using a fluorometer (FIG. 6A) and hemocytometer (FIG. 6B). Readings from the fluorometer showed that, upon administration of DHFR-specific PPMO, there were 83% fewer parasites 96 hours post-infection (FIG. 6A, P=$5.2 \times 10^{-6}$, N=10, data from replicate experiments were similar and are shown here combined). As a control, off-target PPMO did not inhibit DHFR in vivo (P=0.65). Numbers of parasites measured using a hemocytometer indicated that there was a 97% reduction in number of viable parasites after administering PPMO specific to DHFR (FIG. 6B, P=$1.3 \times 10^{-10}$, N=10, data from replicate experiments were similar and shown here are combined).

PPMO inhibit their target frames in a highly sequence-specific manner. A PPMO of 25 bases long was designed as it previously was shown that there has to be a minimum of 14 consecutive bases of sequence conservation for PPMO to be inhibitory (Summerton JE (2007); *Current Topics in Medicinal Chemistry* 7:651-660). This minimum inhibitory length requirement is more stringent than the 9 consecutive bases required for siRNA inhibition to be successful (bases 2 to 8 for recognition and bases 9 to 12 for cleavage of RNA target). Because of PPMO greater minimum length requirement, they have less off-target effects than other inhibitory strategies. Specifically, herein we demonstrate that PPMO targeting YFP, luciferase, DHFR, ENR and an AP2XI-3 transcription factor reduced these protein products and/or reduced parasite replication. Kinetics of YFP-specific PPMO demonstrated that time between 2 to 18 hours after infection that PPMO are added does not alter effect of PPMO. In addition to being effective against Type I RH-YFP parasites, PPMO targeting YFP expression were also effective in Type II Prugneaud tachyzoites stably transfected with YFP.

Uracil incorporation assay demonstrated that DHFR-specific PPMO successfully inhibited tachyzoite replication, a phenotype expected when knocking down DHFR. This assay characterized PPMO as inhibitors against synthesis of specific, essential genes. Successful knock down of fluorescence, luminescence, and a known essential gene was a first proof of concept that established PPMO as a new, sequence-specific knockdown system that can cross multiple membranes to inhibit gene products within intracellular tachyzoites. Antisense oligomers against another enzyme and a transcription factor also were successful. PPMO specific to ENR or AP2XI-3 successfully reduced parasite replication. Effective inhibition of ENR and AP2XI-3 not only suggested that their gene products are essential for tachyzoite replication, but it also demonstrated that this novel inhibitory approach in tachyzoites could be an expeditious tool to screen large numbers of genes for quick target validation. Effect of reducing ENR and AP2XI-3 using transductive peptide-conjugated oligomers underscores that this approach is paradigm-shifting because it opens potential for abrogating any molecular target. Inhibiting transcription factors is difficult through other means. Successful inhibition of ENR demonstrated that PPMO are effective in inhibiting an enzyme of Type II FAS. In the case of abrogating ENR, PPMO targeting ENR were able to cross HFF membranes, parasitophorous vacuole that surrounds replicating intracellular parasites, and parasite membranes. It will be of interest in future studies to determine where ENR is, when it is inhibited, and whether PPMO can cross the four membranes that enclose the apicoplast or other organelles.

The current invention is useful because of the disease burden of *T. gondii* infection, broad applicability of the novel approach for validation of gene function, and potential of the approach to be developed into a widely used therapeutic modality to treat a variety of diseases, including other apicomplexan infections.

The present invention, in one embodiment, provides a means to inhibit parasite molecular targets in tissues such as retina. Substantial reductions in parasite viability evident in vivo demonstrated that PPMO could be used to target *T. gondii*'s essential genes in animal models. Although PPMO was quite effective in mice it was with delivery to a location where the parasite was replicating. In terms of therapeutic potential, PPMO have potential to enter retina and could thereby act as a medicine by inhibiting parasite growth with topical application to the eye.

In another embodiment, the invention provides therapy for parasite infections in the brain. It is known that transductive peptides with N terminal RVG to target acetylcholine receptor can cross the blood brain barrier and carry inhibitory molecules to parasites into brain. Intravenous and intranasal deliveries also have been found to be feasible. This work provides a new paradigm for solving certain previously unsolvable biological problems and for development of novel therapeutic approaches for diseases caused by *T. gondii*. In addition, PPMO could inhibit latent bradyzoites. A model system of delivery to bradyzoites was developed earlier by conjugating a small molecule inhibitor to octaarginine. This peptide delivered molecular cargos across cyst walls and into dormant parasites and their nucleus.

The PPMO system is able to deliver cargo across multiple membranes to intracellular parasites and inhibit various targets. Nonetheless, the system in its present form as a Vivo-PMO™ (Gene Tools, Corvalis, Oreg.) has a narrow therapeutic-toxic ratio. It causes toxicity to host cells, at high concentrations. Thus, this anti-sense system requires further optimization. The toxicity originates from the current transductive peptide, known as the Vivo-porter™. An effective way to eliminate this toxicity and expand the therapeutic range of PPMO is to change the transductive peptide, creating a higher therapeutic-toxic ratio. Moving toward a stable, versatile, robust, less toxic, inhibitor against *T. gondii*, our preliminary data demonstrate that the $(RXR)_4BX$ peptide as part of the ENR PPMO is effective and not toxic at 20 µM (FIG. 9).

Such PPMO or PMO inhibitors have recently entered human clinical trials for Duchenne's muscular dystrophy and to treat Ebola and Marburg virus infections (Moulton HM (2012); *Methods Mol. Biol.* 867:407-414; Delcroix M, Riley L W (2010); *Pharmaceuticals* 3:448-470; Swenson D L, et al. (2009); *Antimicrob Agents Chemother.* 53:2089-2099; Warren T K, et al. (2010); *Nature Medicine* 16:991-994; Kinali M, et al. (2009) *Lancet Neurol.* 8:918-928). In these trials the PPMOs have been found to be stable, safe, effective, and non-immunogenic. This underscores the promise and unique suitability of this approach for the treatment of the devastating diseases caused by *T.gondii*.

Principles and Design of PPMO and PPMO Sequences. We summarize herein the guidelines used for designing PPMO (Moulton JD, Jiang S (2009); *Molecules* 14:1304-1323). PMO of about 5 to about 50 monomeric units are disclosed herein as effective against apicomplexan parasites. PMO of 25 monomeric units is preferable. They can be decreased by a few bases as needed. Shorter oligomers are better for high CG content. Lower CG means that the oligomers' affinities might be too low to block processes, whereas higher CG content favors non-specific binding of subsequences. PMO having lower CG for organisms living below 37° C. are preferred. PMO of the invention contain from about 1 to about 36% G. PMO of the invention may not contain more than three G in a row. No G or A is allowed at the 3' end of a modified oligo is avoided as these may decrease coupling efficiency of the modification.

Upstream (5'-UTR) sequences can be targeted and are usually successful. A morpholino can target anywhere between the 5' cap and the start codon. It also can extend downstream into the coding sequence as long as the start codon is covered. The reason this works is related to the steps at the beginning of translation. A group of proteins and the small ribosomal subunit bind at the 5' cap and then other initiation factors bind, forming the initiation complex. The initiation complex scans through the UTR to the start codon. At the start codon the large subunit binds, the initiation factors dissociate and translation proceeds through the coding region. Interfering with the initiation complex by binding a morpholino to the UTR prevents the initiation from reaching the start codon, but once the large subunit binds and forms an entire ribosome then a morpholino oligomer cannot stop its progression. In the latter case, the ribosome just displaces the downstream oligo from the mRNA and reads through. This is why the targetable region for translation blocking extends from the 5' cap to the start +25 bases.

There are two reasons why targeting at the start is preferable. First, the quality of sequencing deposited in public databases is often poor in the UTR. Sometimes, cloning vector sequences are reported as being in the UTR. Second, though rare in vertebrate genomes, internal ribosome entry sites (IRES) do exist and can allow a ribosome to "short-circuit" a morpholino-blocked target. Therefore, when selecting oligomer sequences, it is preferable to start at the start codon and analyze the possible oligomers in that region.

TABLE 1

PMO Sequences

| Name | Sequence | SEQ ID NO |
|---|---|---|
| YFP-PMO | agctagatTCTAAAATGGTGAGCAAGGGCGAGc | 1 |
| Luciferase-PMO | gatggctGTCATGGAAGACGCCAAAAACATAaagaaa | 2 |

TABLE 1-continued

PMO Sequences

| Name | Sequence | SEQ ID NO |
|---|---|---|
| DHFR-PMO | ctggGAAGATGCAGAAACCGGTGTCTGgtcgtc | 3 |
| ENR-PMO | aaatcgAAAATGGTTGGTTTCAAACTCCTCaccctc | 4 |
| AP2-PMO | cgcgTCTGTTCCGTGCCGCGATGGAGTcgga | 5 |
| Off-Target PMO | TATAAATTGTAACTGAGGTAAGAGG | 6 |
| HIF-1 PMO | ACATCGCGGGGACCGATTCACCATG | 7 |
| VEGF-PMO | GCGATGCGGGGCTGCTGCAATGAC | 8 |

PPMO sequence is bolded; starting codon is underlined; sequences before and after the target genes, which are not included in PPMO designs, are indicted in lowercase letters.

TABLE 2

Transductive Peptide Sequences

| Name | Sequence | SEQ ID NO |
|---|---|---|
| Tat | YGRKKRRQRRRPQ | 9 |
| Tat-R | YGRRRRRQRRRPQ | 10 |
| Tat-RF | YGRRRRRQFLIRRRPQ | 11 |
| R8 | RRRRRRRR | 12 |
| R6 | RRRRRR | 13 |
| P7 | (RXR)4 | 14 |
| Angiopep2 | TPPYGGCRGKRNNPKTEEY | 15 |
| Pip6 | RXRRBRRXRYQFLIRXRBRXRB | 16 |
| RVG | YTIWMPENPRPGTPCDIFTNSRGKRASNG | 17 |
| RVG-9R | YTIWMPENPRPGTPCDIFTNSRGKRASNGGGGRRRRRRRRR | 18 |

As used herein, the term "PPMO" is defined as a PMO chemically derivitized with a transductive peptide. Such derivitization can be accomplished by one with skill in the art. For example conjugation may be accomplished by the methods disclosed in US Pre-grant Patent Application 2005/018213. PPMO of the invention include, but are not limited to, constructs made from conjugation of PMO SEQ ID NO 1 through SEQ ID NO 5, SEQ ID NO 7, and SEQ ID NO 8 wherein the transductive peptides include, but are not limited to SEQ ID NO 9 through SEQ ID NO 18. It will be appreciated that other PMO designed and prepared by one with skill in the art, directed to RNA encoding proteins essential to apicomplexan parasites, or implicated in diseases of the eye, can be conjugated to transductive peptides and such constructs are within the scope of the invention.

It is an object of the invention to provide a method of prophylaxis or treatment of disorders of the eye by contacting an animal in need of such treatment with an effective amount of PMO or PPMO of the invention. In one embodiment, the disorder of the eye is adult macular degeneration. In another embodiment, said disorder is diabetic retinopathy. In still another embodiment, said disorder is infection by an apicomplexan parasite. In one non-limiting example, the apicomplexan parasite is *T. gondii*. As used herein, "effective amount" refers to that concentration, weight, or volume of a composition of the invention which provides prophylaxis or mitigates, ameliorates, mitigates, lessens, or cures said disorder, as determined by one or more practitioners with skill in the art. It is recognized that the effective amount may be determined by one or more administration of the composition.

It is another object of the present invention to provide a method of prophylaxis or treatment of apicomplexan infection of the brain.

It is still another object of the invention to provide a method of prophylaxis or treatment of apicomplexan infection wherein the infection is transferred from a pregnant woman to the fetus during gestation.

As used herein, the term "regimen of mediation" of disease refers to administration of compositions of the invention for the purpose of preventing the onset of disease (herein "prophylaxis") or mitigating, ameliorating, lessening, inhibiting, or curing disease (herein "treatment").

In one embodiment, a composition comprising at least one PMO or PPMO of the invention is administered in an amount which effectively accomplishes the desired prophylaxis or treatment.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing one or more compounds of the invention and a pharmaceutically acceptable carrier. By "pharmaceutically acceptable" it is meant the carrier, diluent or excipient must be devoid of intrinsic biological activity, and be compatible with the other ingredients of the formulation and not deleterious to the recipient thereof.

The terms "administration of" and or "administering" a compound should be understood to mean providing a PMO or PPMO of the invention or a composition containing one or more PMO or PPMO of the invention to an individual or animal in need of treatment by a route generally accepted by those with skill in the art. Routes of such administration include, but are not limited to, oral, buccal, sublingual, inhalation, topical, transcutaneous, intravenous, subcutaneous, intraperitoneal, transdermal, intracerebroventricular, intrathecal, intracerebral implant, and depot implant. In one embodiment, the composition is intended to be administered topically to the eye of the individual or animal in need.

The pharmaceutical compositions for the administration of the compounds of the invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

In some embodiments, compositions of the invention are administered orally.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874, to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

In some embodiments, compositions of the invention are aqueous suspensions.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

In some embodiments, compositions of the invention are oily suspensions.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, flavoring and coloring agents.

The pharmaceutical compositions may be in the form of sterile injectable aqueous solutions, micellar formulations or oleaginous suspensions. Suspensions may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. The pharmaceutical compositions for use as sterile injectable solutions may be colloidal compositions consisting of polymeric micelles which contain within compounds of the invention (U.S. Pat. No. 6,338,859 to Leroux, J. et al 2000).

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

For topical use, creams, ointments, jellies, solutions or suspensions, etc., containing the compounds of the invention are employed. It is intended that topical application according to the present invention shall include mouth washes, dentifrices, and gargles.

In some embodiments, compositions of the PMO or PPMO of the invention is administered with another bioactive substance, wherein the bioactive substance is an antiviral, antibiotic, antifungal, or anti-parasitic agent.

In some embodiments, the composition of PMO or PPMO comprises polyethylene glycol.

In some embodiments of the invention, the PMO or PPMO are contained within or associated with liposomes.

The pharmaceutical compositions of the present invention may be administered to the ocular surface via a pump-catheter system, or released from within a continuous or selective release device such as, e.g., membranes such as, but not limited to, those employed in the Ocusert™ System (Alza Corp, Palo Alto, Calif.). The pharmaceutical compositions can be incorporated within, carried by or attached to contact lenses which are then worn by the subject. The pharmaceutical compositions can be sprayed onto ocular surface. The pharmaceutical compositions of the invention may be delivered by a biodegradable intraocular implant device.

As used herein, the term "ocular delivery" means contacting the eye of an animal in need of prophylaxis or treatment with a composition of the invention wherein said composition comprises a formulation chosen from the set consisting of aqueous suspension, oily suspension, liposome preparation, sterile aqueous solution, gel, hydrogel, nanoparticle preparation, poly(lactic acid-co-glycolic acid) (PLGA) preparation, and microparticles. Such compositions may also comprise excipients as described above.

In some embodiments, the composition of PMO or PPMO comprises liquid drops, liquid wash, gel, hydrogel, ointment, or spray.

In some embodiments, compositions of the invention are administered as eye drops.

Eye drops may be prepared by dissolving the active ingredient in a sterile aqueous solution such as physiological saline, buffering solution, etc., or by combining powder compositions to be dissolved before use. Other vehicles may be chosen, as is known in the art, including but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

In the prophylaxis or treatment of infection caused by an apicomplexan parasite using the method of the invention an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets, capsules, caplets, or pills containing 1.0 to 1000 milligrams of the active ingredient, particularly 1.0, 5.0, 10, 15. 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day. This dosage regimen may be adjusted by healthcare providers with knowledge and skill in the art to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For prophylaxis or treatment of diseases of the eye not caused by parasite infection, as described herein, appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets, capsules, caplets, or pills containing 1.0 to 1000 milligrams of the active ingredient, particularly 1.0, 5.0, 10, 15. 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day. This dosage regimen may be adjusted by healthcare providers with knowledge and skill in the art to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

EXAMPLES

PMO and PPMO preparation. PMO and PPMO were synthesized at Gene Tools LLC (Philomath, Oreg.). PMO oligomers were prepared by standard means known by those skilled in the art, and may be synthesized by the method of Summerton and Weller (Antisense Nucleic Acid Drug Dev 1997; 7(3), 187-195.) Peptides may be conjugated to PMO using the method disclosed in US Pre-grant Patent Application 2005/018213.

Example 1

Cell Culture

Human foreskin fibroblasts (HFF) were cultured in Iscove's Modified Dulbecco's Medium (IMDM) supplemented with 10% heat-inactivated Fetal Bovine Serum (Invitrogen), 1% Glutamax and 1% PSF. When conducting knockdown assays, medium was aspirated and changed to IMDM free of Phenol Red supplemented with 10% heat-inactivated FBS, 1% Glutamax and 1% PSF. Parasites were resuspended in Phenol-free medium as well.

Example 2

PPMO Knockdown

When knocking down YFP fluorescence, DHFR, ENR and AP2XI-3 gene products in Type I RH tachyzoites, HFF were seeded in black, flat-bottom 96-well microplates. Each well was infected with 2,000 Type 1 *T. gondii* parasites that are a clonally derived stable line expressing cystolic YFP (Gubbels M, Li C, Striepen B (2003); *Antimicrob. Agents Chemother.* 47:309-316). When inhibiting YFP fluorescence in Type II Prugneaud parasites stably transfected with YFP, HFF were infected with 3,500 instead of 2,000 tachyzoites, as Type II parasites grow slower than Type I tachyzoites. After two hours of infection, wells were separately treated with 1.5 µM, 2.5 µM, 3.75 µM, and 5 µM of PPMO targeting the correlating gene product. All wells were rocked gently to ensure even distribution of oligomers without disturbing HFF monolayers. When knocking down luciferase luminescence, fibroblasts were seeded in white, opaque 96-well microplates. Each well was infected with 3,500 Type 2 *T. gondii* parasites that are stably transfected with luciferase. After two hours of infection, wells were separately treated with 1.5 µM, 2.5 µM, 3.75 µM, and 5 µM of luciferase-specific and off-target PPMO. Off-target PPMO was used in all knockdown experiments as a control.

Example 3

Measuring YFP and Luminescence 96 hours after parasite infection, fluorescence and luminescence were respectively measured for YFP and luciferase inhibition using Synergy™ H4 Hybrid Multi-Mode Microplate Reader. This time frame was chosen because a reasonable estimate of the'time that PPMO remain effective in cells and animals has been found to be 4 to 5 days in earlier work (Wells DJ (2008); *Br J Pharmacol.* 154:623-631). YFP fluorescence was read at 540 nm. Luciferin stock solution was created by diluting 33 mg of luciferin potassium salt in 1 mL of nuclease-free, deionized, distilled water. Stock solution was diluted 1:20, and 20 µL was added to every well. 30 minutes after adding in luciferin, luminescence was read 10 seconds per well at 420 nm, and at 37° C. for optimal signal.

Example 4

Immunofluorescence

HFF were grown on coverslips in 24-well multi-well plates. When confluent, they were infected with $10^3$ YFP-transfected RH tachyzoites with or without 3.75 μM of YFP-, DHFR- or ENR-specific PPMO. Medium was aspirated under sterile condition after 48 hours of treatment. HFF were then treated with 3% paraformaldehyde for 30 minutes at room temperature. They were then permeabilized with 0.2% TritonX-100 in PBS at room temperature for 10 minutes, and blocked with 0.2% TritonX-100 and 3% BSA in PBS overnight at 4° C. Antibodies specific to DHFR or ENR, diluted 1:500 were in buffer. They were further blocked with Texas Red secondary antibody diluted 1:1000 in blocking solution. DAPI stain was diluted 1:1000 in blocking solution and applied for 1 hour at room temperature. Cells were rinsed three times in PBS, and coverslips were mounted using nail polisher. Slides were examined using Nikon Eclipse Ti.

Example 5

Assays to Assess Effects of PPMO on *T. gondii* Tachyzoite Replication in Vitro

Tritiated uracil uptake assays were conducted as previously described (Mui E, et al. (2005) *Antimicrob. Agents Chemother.* 49:3463-3467; Mack DG & McLeod R (1984); *Antimicrob. Agents Chemother.* 26:26-30; Roberts F, et al (1998); *Nature* 393:801-805).

Example 6

Assays to Assess Effects of PPMO on Host Cell Viability in Vitro

HFF viability was measured using Premixed WST-1 Cell Proliferation Reagent. Tetrazolium salt WST-1 is converted to formazan in mitochondria only in viable cells. Viability assays involving WST-1 Reagent work by measuring the absorption of formazan dye in cells. High absorption signifies cell viability. The numbers of viable cells positively correlates with the quantities of formazan dye absorbed.

Example 7

Folic Acid Rescue of DHFR Knock Down

40% of Sodium Hydroxide was diluted 1:10 in Iscove's Modified Dulbecco's Medium without Phenol Red. 0.5 g of folic acid was incrementally dissolved in every 10 mL of diluted Sodium Hydroxide, resulting in 113 mM folic acid stock solution. Stock solution was serially diluted and added to wells of 96-well plates. Fluorescence was measured 96 hours post-infection.

Example 8

Effects of PPMO on Tachyzoites In Vivo 20-week old C57BI6J HLA A2 female mice were each infected with $10^3$ YFP-transfected RH parasites. Mice were injected intraperitoneally with 12.5 mg of DHFR-specific PPMO. Further treatment was given 24 hours after infection, for a total of 2 PPMO doses. Intraperitoneal fluid was collected 96 hours post-infection and parasite fluorescence and numbers were measured using a fluorometer and hemocytometer respectively.

Example 9

Analysis of Data and Statistics

For analysis of effect of YFP PPMO for in vitro studies, statistical analysis comparing experimental group data to PBS control was with Student's t test. No adjustments for multiple comparisons were made. For in vivo experiments an initial ANOVA was performed when P<0.000001, pair wise T comparisons were performed using Student's t test. Regression analysis was with Coefficient of determination ($R^2$).

We claim:

1. A method of treatment of disease comprising contacting a patient with an effective amount of a pharmaceutical composition comprising a PMO oligonucleotide analog, wherein said PMO is an antisense phosphorodiamidate morpholino oligomer chosen from the set consisting of SEQ ID NO 3, SEQ ID NO 4, SEQ ID NO 5, SEQ ID NO 7 and SEQ ID NO 8.

2. The method of claim 1 wherein said disease is infection by an apicomplexan parasite, and said PMO is SEQ ID NO 4.

3. The method of claim 1 wherein said disease is infection by an apicomplexan parasite, and said PMO is SEQ ID NO 5.

4. The method of claim 1 wherein said disease is infection by *Toxoplasma gondii*, and said PMO is SEQ ID NO 4.

5. The method of claim 1 wherein said disease is infection by *Toxoplasma gondii*, and said PMO is SEQ ID NO 5.

6. A method of treatment of infection by *Toxoplasma gondii* comprising contacting a patient with an effective amount of a pharmaceutical composition comprising a PPMO, wherein said PPMO is constructed by conjugation of a transductive peptide to a PMO oligonucleotide analog, wherein said PMO is an antisense phosphorodiamidate morpholino oligomer chosen from the set consisting of SEQ ID NO 3, SEQ ID NO 4, SEQ ID NO 5, SEQ ID NO 7 and SEQ ID NO 8, and wherein said transductive peptide is chosen from the set consisting of SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, and SEQ ID NO 18.

7. The method of claim 4 wherein said contacting is administration of an ocular formulation to the eye.

8. The method of claim 5 wherein said contacting is administration of an ocular formulation to the eye.

9. The method of claim 1 wherein said contacting is administration of an ocular formulation to the eye.

10. The method of claim 6 wherein said transductive peptide is SEQ ID NO 14 and said PMO is chosen from the set consisting of SEQ ID NO 3, SEQ ID NO 4, SEQ ID NO 5, SEQ ID NO 7 and SEQ ID NO 8.

* * * * *

SEQUENCE LISTING

<160> NUMBER OF SEQ ID NOS: 18

<210> SEQ ID NO 1
<211> LENGTH: 33
<212> TYPE: DNA
<213> ORGANISM: Artificial
<220> FEATURE:
<223> OTHER INFORMATION: Synthetic Antisense Phosphorodiamidate
      Morpholino Polynucleotide Analog

<400> SEQUENCE: 1
agctagattc taaaatggtg agcaagggcg agc                               33

<210> SEQ ID NO 2
<211> LENGTH: 37
<212> TYPE: DNA
<213> ORGANISM: Artificial
<220> FEATURE:
<223> OTHER INFORMATION: Synthetic Antisense Phosphorodiamidate
      Morpholino Polynucleotide Analog

<400> SEQUENCE: 2
gatggctgtc atggaagacg ccaaaaacat aaagaaa                           37

<210> SEQ ID NO 3
<211> LENGTH: 33
<212> TYPE: DNA

```
<213> ORGANISM: Artificial
<220> FEATURE:
<223> OTHER INFORMATION: Synthetic Antisense Phosphorodiamidate
      Morpholino Polynucleotide Analog

<400> SEQUENCE: 3
ctgggaagat gcagaaaccg gtgtctggtc gtc                               33

<210> SEQ ID NO 4
<211> LENGTH: 36
<212> TYPE: DNA
<213> ORGANISM: Artificial
<220> FEATURE:
<223> OTHER INFORMATION: Synthetic Antisense Phosphorodiamidate
      Morpholino Polynucleotide Analog

<400> SEQUENCE: 4
aaatcgaaaa tggttggttt caaactcctc accctc                            36

<210> SEQ ID NO 5
<211> LENGTH: 31
<212> TYPE: DNA
<213> ORGANISM: Artificial
<220> FEATURE:
<223> OTHER INFORMATION: Synthetic Antisense Phosphorodiamidate
      Morpholino Polynucleotide Analog

<400> SEQUENCE: 5
cgcgtctgtt ccgtgccgcg atggagtcgg a                                 31

<210> SEQ ID NO 6
<211> LENGTH: 25
<212> TYPE: DNA
<213> ORGANISM: Artificial
<220> FEATURE:
<223> OTHER INFORMATION: Synthetic Antisense Phosphorodiamidate
      Morpholino Polynucleotide Analog

<400> SEQUENCE: 6
tataaattgt aactgaggta agagg                                        25

<210> SEQ ID NO 7
<211> LENGTH: 25
<212> TYPE: DNA
<213> ORGANISM: Artificial
<220> FEATURE:
<223> OTHER INFORMATION: Synthetic Antisense Phosphorodiamidate
      Morpholino Polynucleotide Analog

<400> SEQUENCE: 7
acatcgcggg gaccgattca ccatg                                        25

<210> SEQ ID NO 8
<211> LENGTH: 25
<212> TYPE: DNA
<213> ORGANISM: Artificial
<220> FEATURE:
<223> OTHER INFORMATION: Synthetic Antisense Phosphorodiamidate
      Morpholino Polynucleotide Analog

<400> SEQUENCE: 8
gcgatgcggg ggctgctgca atgac                                        25

<210> SEQ ID NO 9
<211> LENGTH: 13
<212> TYPE: PRT
<213> ORGANISM: Artificial
<220> FEATURE:
```

<223> OTHER INFORMATION: Synthetic Transductive Peptide

<400> SEQUENCE: 9

Tyr Gly Arg Lys Lys Arg Arg Gln Arg Arg Pro Gln
1               5                   10

<210> SEQ ID NO 10
<211> LENGTH: 13
<212> TYPE: PRT
<213> ORGANISM: Artificial
<220> FEATURE:
<223> OTHER INFORMATION: Synthetic Transductive Peptide

<400> SEQUENCE: 10

Tyr Gly Arg Arg Arg Arg Arg Gln Arg Arg Pro Gln
1               5                   10

<210> SEQ ID NO 11
<211> LENGTH: 16
<212> TYPE: PRT
<213> ORGANISM: Artificial
<220> FEATURE:
<223> OTHER INFORMATION: Synthetic Transductive Peptide

<400> SEQUENCE: 11

Tyr Gly Arg Arg Arg Arg Arg Gln Phe Leu Ile Arg Arg Pro Gln
1               5                   10                  15

<210> SEQ ID NO 12
<211> LENGTH: 8
<212> TYPE: PRT
<213> ORGANISM: Artificial
<220> FEATURE:
<223> OTHER INFORMATION: Synthetic Transductive Peptide

<400> SEQUENCE: 12

Arg Arg Arg Arg Arg Arg Arg Arg
1               5

<210> SEQ ID NO 13
<211> LENGTH: 6
<212> TYPE: PRT
<213> ORGANISM: Artificial
<220> FEATURE:
<223> OTHER INFORMATION: Synthetic Transductive Peptide

<400> SEQUENCE: 13

Arg Arg Arg Arg Arg Arg
1               5

<210> SEQ ID NO 14
<211> LENGTH: 12
<212> TYPE: PRT
<213> ORGANISM: Artificial
<220> FEATURE:
<223> OTHER INFORMATION: Synthetic Transductive Peptide
<220> FEATURE:
<221> NAME/KEY: MISC_FEATURE
<222> LOCATION: (2)..(11)
<223> OTHER INFORMATION: Xaa = 6-aminohexanoic acid

<400> SEQUENCE: 14

Arg Xaa Arg Arg Xaa Arg Arg Xaa Arg Arg Xaa Arg
1               5                   10

<210> SEQ ID NO 15
<211> LENGTH: 19
<212> TYPE: PRT

```
<213> ORGANISM: Artificial
<220> FEATURE:
<223> OTHER INFORMATION: Synthetic Transductive Peptide

<400> SEQUENCE: 15

Thr Pro Pro Tyr Gly Gly Cys Arg Gly Lys Arg Asn Asn Pro Lys Thr
1               5                   10                  15

Glu Glu Tyr

<210> SEQ ID NO 16
<211> LENGTH: 22
<212> TYPE: PRT
<213> ORGANISM: Artificial
<220> FEATURE:
<223> OTHER INFORMATION: Synthetic Transductive Peptide
<220> FEATURE:
<221> NAME/KEY: MISC_FEATURE
<222> LOCATION: (2)..(22)
<223> OTHER INFORMATION: B = Asx
<220> FEATURE:
<221> NAME/KEY: MISC_FEATURE
<222> LOCATION: (2)..(22)
<223> OTHER INFORMATION: B = Asx
<220> FEATURE:
<221> NAME/KEY: MISC_FEATURE
<222> LOCATION: (2)..(22)
<223> OTHER INFORMATION: X = 6-aminohexanoic acid

<400> SEQUENCE: 16

Arg Xaa Arg Arg Asx Arg Arg Xaa Arg Tyr Gln Phe Leu Ile Arg Xaa
1               5                   10                  15

Arg Asx Arg Xaa Arg Asx
            20

<210> SEQ ID NO 17
<211> LENGTH: 41
<212> TYPE: PRT
<213> ORGANISM: Artificial
<220> FEATURE:
<223> OTHER INFORMATION: Synthetic Transductive Peptide

<400> SEQUENCE: 17

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly Gly Gly Gly
            20                  25                  30

Arg Arg Arg Arg Arg Arg Arg Arg Arg
        35                  40

<210> SEQ ID NO 18
<211> LENGTH: 41
<212> TYPE: PRT
<213> ORGANISM: Artificial
<220> FEATURE:
<223> OTHER INFORMATION: Synthetic Transductive Peptide

<400> SEQUENCE: 18

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly Gly Gly Gly
            20                  25                  30

Arg Arg Arg Arg Arg Arg Arg Arg Arg
        35                  40
```